US011600203B2

(12) United States Patent
Sedberry et al.

(10) Patent No.: US 11,600,203 B2
(45) Date of Patent: Mar. 7, 2023

(54) NON-LETHAL WEAPONS MODULAR HUMAN SURROGATE TESTING DEVICE AND METHOD

(71) Applicant: CFD Research Corporation, Hunstville, AL (US)

(72) Inventors: David Keith Sedberry, Huntsville, AL (US); Vincent J. Harrand, Huntsville, AL (US); Phillip E. Whitley, Huntsville, AL (US); Andrzej Przekwas, Huntsville, AL (US)

(73) Assignee: CFD Research Corporation, Huntsville, AL (US)

( * ) Notice: Subject to any disclaimer, the term of this patent is extended or adjusted under 35 U.S.C. 154(b) by 490 days.

(21) Appl. No.: 16/696,997

(22) Filed: Nov. 26, 2019

(65) Prior Publication Data

US 2021/0280088 A1 Sep. 9, 2021

Related U.S. Application Data

(60) Provisional application No. 62/780,806, filed on Dec. 17, 2018.

(51) Int. Cl.
*G09B 23/34* (2006.01)
*G01N 33/00* (2006.01)
(Continued)

(52) U.S. Cl.
CPC ............ *G09B 23/34* (2013.01); *G01D 21/02* (2013.01); *G01N 33/00* (2013.01);
(Continued)

(58) Field of Classification Search
CPC ........ G09B 23/34; G01N 33/00; G01D 21/02; F41H 13/0075; F41H 13/0081; F41H 13/0056
(Continued)

(56) References Cited

U.S. PATENT DOCUMENTS 5,528,943 A * 6/1996 Smrcka ................ G09B 23/281
73/866.4
5,648,915 A * 7/1997 McKinney ............. G09B 23/30
73/865.1
(Continued)

FOREIGN PATENT DOCUMENTS

CN 105352364 * 2/2016
CN 107131988 * 9/2017
(Continued)

*Primary Examiner* — Robert R Raevis
(74) *Attorney, Agent, or Firm* — Maschoff Brennan

(57) ABSTRACT

A modular surrogate can include: a body having an external body surface with an anatomical shape, wherein the body includes an internal chamber with at least one port formed in the body extending inwardly; at least one anatomical module having an external module portion and a module stem coupled thereto, the module stem being received into a corresponding module port of the at least one port, the external module portion having an external module surface with an anatomical shape, the external body surface matches with the external module surface to provide a continuous anatomical shape; at least one sensor located in the at least one anatomical module; and at least one controller, wherein when the at least one anatomical module is coupled with the body, the at least one sensor is capable of being operably coupled with the at least one controller.

24 Claims, 7 Drawing Sheets

(51) Int. Cl.
*G01D 21/02* (2006.01)
*F41H 13/00* (2006.01)

(52) U.S. Cl.
CPC ...... *F41H 13/0056* (2013.01); *F41H 13/0075* (2013.01); *F41H 13/0081* (2013.01)

(58) Field of Classification Search
USPC .......... 73/11.01, 12.01, 12.08, 865.1, 865.4, 73/865.6, 865.8, 866.4, 432.1; 434/262, 434/267–272, 274, 275
See application file for complete search history.

(56) References Cited

U.S. PATENT DOCUMENTS

| | | | | |
|---|---|---|---|---|
| 7,204,165 | B1* | 4/2007 | Plaga | G01N 3/30 |
| | | | | 73/12.01 |
| 2018/0136083 | A1* | 5/2018 | Wang | G09B 23/34 |
| 2018/0170416 | A1* | 6/2018 | Vogt | G01M 17/0078 |

FOREIGN PATENT DOCUMENTS

| | | | |
|---|---|---|---|
| DE | 102015004536 | * | 6/2016 |
| EP | 1388833 | * | 2/2004 |
| GB | 2344922 | * | 6/2000 |
| JP | 2002257653 | * | 9/2002 |
| WO | 20141118496 | * | 8/2014 |

* cited by examiner

NON-LETHAL WEAPONS MODULAR HUMAN SURROGATE TESTING DEVICE AND METHOD

CROSS-REFERENCE

This patent application claims priority to U.S. Provisional Application No. 62/780,806 filed Dec. 17, 2018, which provisional is incorporated herein by specific reference in its entirety.

GOVERNMENT RIGHTS

This invention was made with government support under Joint Non-Lethal Weapons Directorate (JNLWD) Marine Command (MARCOR) Contract No. M67854-14-C-6501. The government has certain rights to the inventions described in this application.

BACKGROUND

The field of non-lethal weapons (NLW) and associated technologies has been emerging over the last two decades as a personnel deterrent. The NLW provide an alternative to lethal force, and are often used to temporarily disorient a target subject without significant or permanent injury to the subject or other subjects in close proximity. Non-lethal exposures (NLE) to stimuli have also come into development for various uses. Human responses to these NLW/NLE are reasonably understood for some stimuli modalities, such as pressure and sound. However, other stimuli from other NLW technologies, such as lasers, RF heating, and the combined effects of multiple stimuli modalities exposed on a human at the same time are not well understood.

Human surrogates for target subjects have existed in evaluating a multitude of events, such as automobile crashes, pilot ejection, and limb/spinal impacts. There are numerous patents that exist for the events described above relating to human surrogates and testing platforms. Some background examples of surrogates include: U.S. Pat. Nos. 3,010,223; 8,725,449; 7,204,165; 3,557,471, and German Patent No. 102016124240B4, which are incorporated herein by specific reference in their entirety. Most of the current technologies have been based on creating an anatomical human surrogate or parts (e.g., head, shoulder, neck, spine, etc.) for use in measuring one event or exposure such as pressure or impact. However, the current surrogates are often only configured for a single stimuli and are not adaptable.

Therefore, it would be advantageous to have a complex surrogate that can be used for multiple stimuli, and which can be adaptable.

SUMMARY

In some embodiments, a modular surrogate can include: a body having an external body surface with an anatomical shape, wherein the body includes an internal chamber with at least one port formed in the body extending inwardly from the external body surface; at least one anatomical module having an external module portion and a module stem coupled to the external module portion, the module stem being configured to be received into a corresponding module port of the at least one port, the external module portion having an external module surface with an anatomical shape, when the module stem is located in the module port, the external body surface matches with the external module surface to provide a continuous anatomical shape; at least one sensor located in the at least one anatomical module; and at least one controller, wherein when the at least one anatomical module is coupled with the body, the at least one sensor is capable of being operably coupled with the at least one controller. In some aspects, the body has an anatomical shape of at least one of a head or a torso. In some aspects, the body has an anatomical shape of a head and is configured as a head module, the modular surrogate further comprising a second body having an anatomical shape of a torso configured as a torso module. In some aspects, the body has an anatomical shape of a torso and is configured as a torso module, the modular surrogate further comprising a second body having an anatomical shape of a head configured as a head module.

In some embodiments, a modular surrogate can include: a head module having a head body having an external body surface with an anatomical shape of a head, wherein the head body includes an internal chamber with at least one eye port and at least one ear port formed in the body extending inwardly from the external body surface; at least one eye module having an external eye portion and a module stem coupled to the external eye portion, the module stem being configured to be received into a corresponding eye port of the at least one eye port, the external eye portion having an external eye surface with an eye shape, when the module stem is located in the module port, the external eye surface matches with the external module surface to provide a continuous anatomical shape; at least one ear module having an external ear portion and a module stem coupled to the external ear portion, the module stem being configured to be received into a corresponding ear port of the at least one ear port, the external ear portion having an external ear surface with an ear shape, when the module stem is located in the module port, the external ear surface matches with the external module surface to provide a continuous anatomical shape; a torso module configured to be linked to the head module; at least one sensor located in the at least one eye module; at least one sensor located in the at least one ear module; at least one sensor located in the torso module; and at least one controller, wherein: when the at least one eye module is coupled with the head module, the at least one sensor in the at least one eye module is capable of being operably coupled with the at least one controller; when the at least one ear module is coupled with the head module, the at least one sensor in the at least one ear module is capable of being operably coupled with the at least one controller; and when the at least one sensor in the torso module is capable of being operably coupled with the at least one controller.

In some embodiments, a method of testing exposure to a stimulus can include: providing a modular surrogate of one of the embodiments; exposing the modular surrogate to at least one stimulus; measuring the at least one stimulus with the at least one sensor to obtain stimulus data; and recording the stimulus data with the controller. In some aspects, the method can include: determining the at least one stimulus; and preparing the modular surrogate such that the at least one sensor measures the at least one stimulus. In some aspects, the method can include the at least one stimulus being at least one of: sound, light, heat, blunt impact, pressure, or electro-muscular stimulation.

In some embodiments, a method of developing a non-lethal exposure with a modular surrogate can include: determining the at least one stimulus of the non-lethal exposure configuring the modular surrogate with at least one sensor for measuring the at least one stimulus; and performing the method steps of one of the embodiments.

In some embodiments, a method of developing a non-lethal weapon with a modular surrogate can include: determining the at least one stimulus of the non-lethal weapon; configuring the modular surrogate with at least one sensor for measuring the at least one stimulus; and performing the method steps of one of the embodiments.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and following information as well as other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

Figure 1:
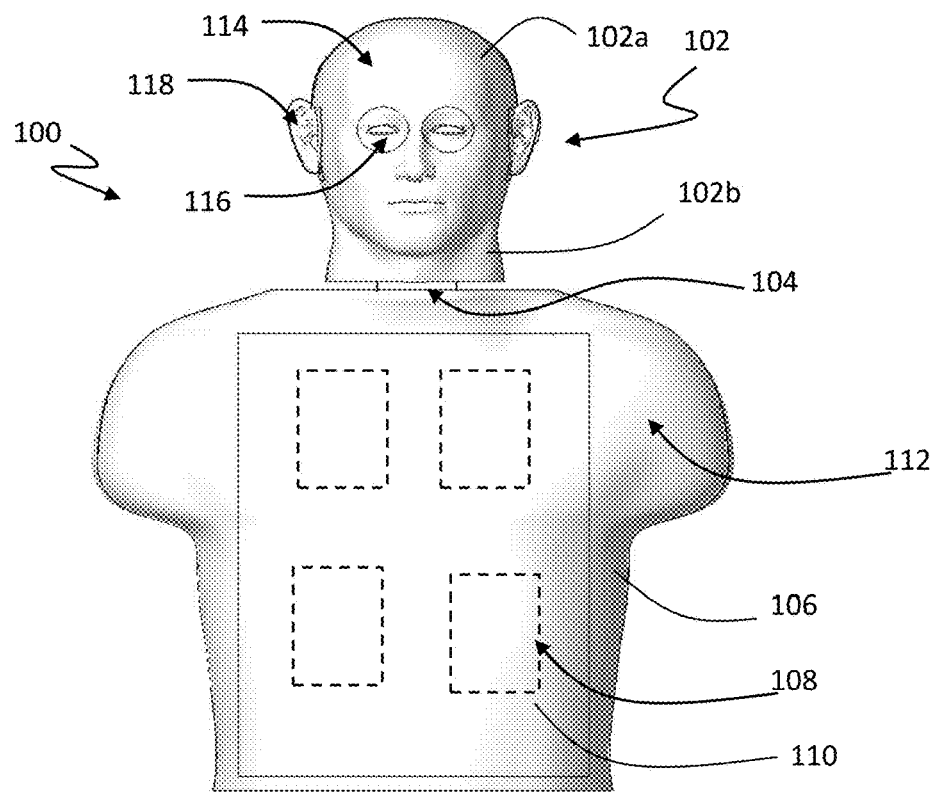
FIG. 1 shows an embodiment of a modular human surrogate.

The subject matter of the figures can include elements and components arranged in accordance with at least one of the embodiments described herein, and which arrangement may be modified in accordance with the disclosure provided herein by one of ordinary skill in the art.

DETAILED DESCRIPTION

In the following detailed description, reference is made to the accompanying drawings, which form a part hereof In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Generally, the present technology includes a modular stimuli monitoring surrogate (MSMS) that has at least one exchangeable module and preferably a plurality of exchangeable modules, each module including at least one sensor for a stimulus. The MSMS can be configured to test one or more stimuli at the same time. The module(s) can be configured with anatomical shapes for improved stimuli monitoring and measuring with realistic features. The MSMS can provide a modular platform for testing that is specifically aimed at evaluating non-lethal weapons (NLW) and non-lethal exposures (NLE) or other similar events to acquire information that can be analyzed to determine human responses relating to pain, injury, and exposure thresholds. The MSMS can include a body shape or portion thereof of any animal, such as human, dog (e.g., for service animals), horse, cat, cow, dolphin, whale or the like for any mammal, fish, reptile, bird or any other animal. The body shape may have module ports for receiving the anatomical modules at anatomically relevant locations, such as the mouth, nose, eyes, ears, or the like, adapted to receive the corresponding anatomical module. An anatomical module can include one or more sensors relevant to measure a stimuli that may impact that specific anatomical body part. The MSMS can include a computer system (e.g., a controller configured as a computer) that can be operably coupled with each sensor so as to receive stimuli data and perform data saving or processing actions, such as those described herein.

In some embodiments, the MSMS can include a human anatomy body shape with one or more anatomical modules with corresponding sensors for different anatomical body parts. The MSMS can include various sensor packages that can be used to evaluate and measure different stimuli, such as the stimuli of a NLW or NLE or other event. The MSMS can receive the stimuli via the sensor and then provide the stimuli data to the computing system for saving, transmitting or otherwise processing the stimuli data to provide relevant data produced in response to a NLE. The modular configuration allows for the MSMS to be outfitted with appropriate anatomical modules and sensor packages for measuring one or multiple stimuli modalities and exposures at the same time (e.g., pressure and sound). This can be useful because many NLWs use multiple stimuli modalities to disorient or disable a human target.

The MSMS can be configured such that the computing system can receive the stimuli data in real time, which can be stored, processed or transmitted to an external computer in real time. The MSMS can provide real time feedback and operational responses to the stimuli. The stimuli data can be compared to real human responses to provide for correlations that can be used to assess a human response.

The MSMS can be used in various industries. The MSMS can be especially suited for use in designing of NLW and NLE devices or during training of operators of NLW or first responders that may be involved in responding to use of a NLW or NLE. As such, the MSMS can be used in any scenario as a surrogate to measure stimuli present in the scenario.

In some embodiments, the MSMS can include one or multiple anatomical modules for each sensor location. The anatomical modules can include one or more sensors to measure stimuli that can act on the anatomical body part mimicked by the anatomical modules.

In some aspects, to measure the consequences of a blast (e.g., pressure) stimuli, anatomical modules can be configured as eyes and/or ears with pressure sensing sensors to measure the amount of pressure received at that anatomical body part during a blast. Mouth modules may be configured to be anatomically correct so as to test the blast on teeth, tongue and throat. Torso, neck, and limb anatomical modules may also include pressure sensors to measure the effects of pressure on any desired area of a body. The pressure sensors can receive pressure and then output pressure data, such as in the form of a signal (e.g., electrical, optical, audio, etc.). The pressure sensors can be used to measure changes in pressure in the fluid environment (e.g., air, water, etc.) or other variables such as fluid/gas flow, speed, water level, and altitude. Pressure sensors can be configured as pressure transducers, pressure transmitters, pressure senders, pressure indicators, piezometers and manometers, among others.

In an example, pressure transducers, in two configurations (tube and pancake), with a 50 psi range can be used because most NLW do not approach this upper threshold of pressure. The pressure transducers can be mounted in the eye module and at the ear module for data collection. For sound, a piezoelectric microphone can be used with an upper end threshold of 190+dB. Microphones can be placed inside the ear module at the tympanic membrane or outside the ear flush with the skin.

In some aspects, to measure the consequences of sound (e.g., acoustic) stimuli, anatomical modules can be configured as ears, but may be any other anatomical part. The acoustic sensors can measure the level of sound, such as in decibels, (e.g., with a microphone) or other measurement type. For example, the acoustic sensor, which can include a microphone, can be placed in the ear module in a location corresponding to the eardrum.

In some aspects, to measure the consequences of light, such as broad spectrum light, whether focused or unfocused or laser light stimuli, the anatomical modules can be configured as eyes, but may be any other anatomical part, such as skin where focused light or laser may generate heat. Accordingly, optical sensors that convert light into a signal may be placed in the eye with the sensor facing out. Any type of optical sensor, such as photoconductive, photovoltaics photodiodes, phototransistors, or others can be used. Multiple optical sensors may be positioned in the eye module. Additionally, temperature sensors may be used in addition to or in place of optical sensors when measuring the thermal consequences of a light stimuli.

The optical sensor can be any optical sensor ranging from photodiodes, to CMOS sensors, to any device capable of measuring a property of light. In an example, the optical sensor instrumentation can include a photodiode, shutter, and optical cable, which can be mounted inside the removable eye module and operably coupled with the controller (e.g., computing system, analog to digital converter, etc.). This system functions much like the human eye where the shutter response can be adjusted based on the type of environment the human surrogate is placed in (light/dark/etc.). As the eye is exposed to broadband or laser light, the shutter closes mimicking the human eye response. The light exposure data can be captured on a separate power meter.

In some aspects, to measure the consequences of electro-muscular disruption (EMD) stimuli, the anatomical part can be at any location, such as face, head, neck, torso, limbs, or specific or general muscles thereof, where the electrical sensor can be appropriately placed to measure the electrical stimuli. Examples of EMD include tasers or other electrical discharge devices.

In an example, an EMD detecting module can include one or more sensor pads (e.g., one sensor pad or six pads). Each sensor pad uses a conductive foam outer layer, which transmits the voltage data through the electrical connections to the rear of the torso where the controller is located, which may also include output cable connectors to physically plug into an external computer, or a transmitter for wireless data transmission. The overall resistance of the system is similar to the human body (approximately 600 Ohm) with step down resistors to ensure the voltage that is sampled is at a safe level for the data acquisition system.

In some aspects, to measure the consequences of laser or radio frequency (RF) heating (e.g., temperature) stimuli, the anatomical part can be at any location, such as face, head, neck, torso, limbs, or portion, where the temperature sensor (e.g., thermocouple, thermistor, resistance temperature detector, infrared temperature sensor, or other) can be appropriately placed to measure the temperature. In an example, a thermocouple can be mounted in an eye module, ear module, or in a removable chest plate.

In some aspects, to measure the consequences of impact (e.g., blunt force) stimuli, the anatomical part can be the head, which is often a target, but can be the face, neck, torso, or limb. The anatomical module can include impact sensors, such as shock or impact sensors. In some examples, the impact sensors can be embedded under the external surface, such as surrogate skin, of the anatomical module.

In an example, areas of importance for blunt impact are often the head and the torso. The head of the MSMS can be outfitted with a 6 DOF sensor placed at the top of the neck, which measures linear and angular movement and loadings using a flexible neck. A modular blunt impact torso can use one pressure sensor (e.g., FIG. 9) or an array of pressure sensors (e.g., FIG. 1 dashed line rectangles) embedded in a soft tissue simulant and an accelerometer placed on the sternum of the torso. The array of sensors can be included in a removable chest plate, and can be changed based on any specific location of interest on the front of the chest.

The MSMS can be configured to be life-like of any anatomical part or the entire anatomy. An example of a head module can include a skull member and realistic skin. Another example can include the head module on a neck and torso in various configurations. The modularity of the MSMS allows for a wide range of different anatomical modules, each having sensor packages of one or more sensors. The sensors can be integrated into the various anatomical modules at anatomically relevant locations where the stimuli is received, and thereby conditioned by the anatomical features thereof. In an example, a modular head can include ports for the mouth, eyes and/or ears, where the ports receive the anatomical module with the sensor packages and are configured to be exchangeable. Also, the entire head may be a module with various sensor packages for the anatomical features thereof, such as including a brain module with sensors, such as pressure, impact, or EMD sensors. For example, for a NLE that uses sound and light as a combined effects NLW, the MSMS can be outfitted with laser sensors in the removable eye modules and acoustic measurement sensors located at the ear modules (e.g., at the tympanic membrane area) inside and outside the removable ear module. These sensors capture the exposure stimuli of the NLE, which can be processed by the computing system of the MSMS in real time for real time analysis or saved on a storage device to be accessed later for analysis. The combination of light and sound stimuli can be tested with the MSMS to determine the effectiveness of the NLW and the human response effect on the target subject.

In some embodiments, the MSMS includes a module head with a skull, an option for realistic skin, a neck, and a torso with multiple sensor configurations based on assessing the consequences of EMD and blunt impact stimuli exposures. The MSMS can include a computer configured as a controller, or can transmit the stimuli data to an external computer that can be used for evaluating the NLE for effectiveness on the target as well as provide real time responses to the stimuli from the MSMS sensors.

In some embodiments, the MSMS can be configured for measuring the stimuli exposure of a NLW from an anatomically accurate human surrogate. The anatomy of the MSMS allows for more realistic scenarios, such as putting clothing (e.g., civilian, military, impact resistant, bullet proof vests, helmets, etc.) on the test surrogate, which adds a layer of realism and accuracy to the response of the test surrogate. Eyewear, helmets, or body armor, such as wearable items that have been developed to protect against some NLW/NLE can be mounted on the head or other body portions of the test surrogate to provide accurate and real world use case testing. The anatomy of the MSMS also enhances the response to NLW/NLE, which are influenced by the curvature of the skin, such as around the eye where reflections and focal points affect exposures to these weapons. Accordingly, anatomical correctness of the MSMS and anatomical modules along with anatomically correct placement of sensors can provide significant improvements in stimuli data collection and processing.

In some embodiments, the MSMS can include a skin surrogate configured as a biofidelic outer layer, which mimics the human skin (e.g., US No. 2017/0011657).

FIG. 1 shows an embodiment of an upper MSMS 100, which includes a head module 102 having a head 102a mounted on a neck 102b, which is coupled through a neck stem 104 to a torso module 106. The torso module 106 can include an internal compartment 108, which can be covered with an anatomical chest plate 110. As shown, the upper MSMS includes a modular human surrogate assembly having: an anatomical head module 102 that includes skin 112 and skull parts 114; a neck stem 104; and a torso module 106. The head module 102 can further include eye modules 116 and ear modules 118. The modular nature of the MSMS allows for a wide range of sensors and instrumentation depending on the type and function of the NLE being evaluated for human response. For example, sensors and instrumentation can be placed in the eye modules 116 and ear modules 118, along the surface of the head module 102, in the neck stem 104 or neck portion of the head module 102, outside and/or inside the torso module 106, and embedded in the skin 112 and skull parts 114.

Figure 1A:
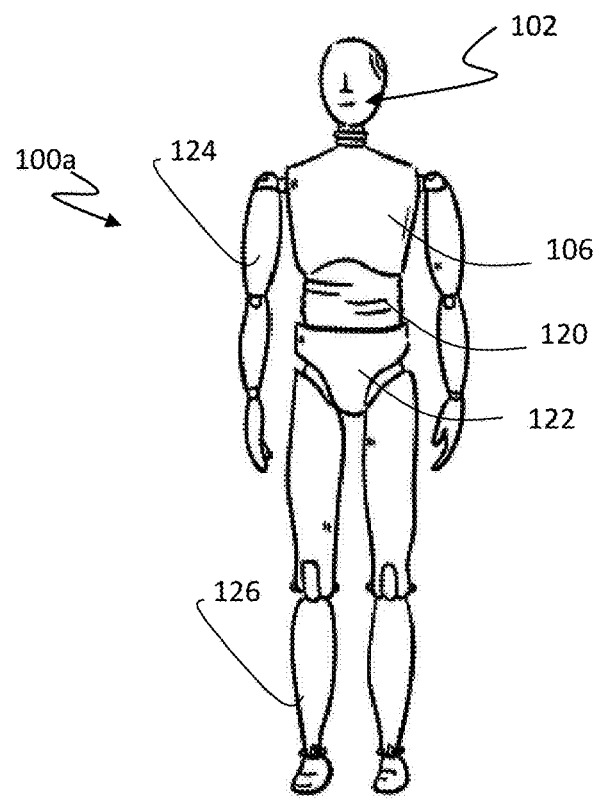
FIG. 1A shows another embodiment of a modular human surrogate.

FIG. 1A shows a full body MSMS 100a having the head module 102, torso module 106, abdomen module 120, pelvic module 122, arm modules 124, and leg modules 126, arranged as illustrated. Each of the modules can have any of the sensors described herein or otherwise known.

The MSMS 100 can include the skin 112, which may be biofidelic with appropriate sensors therein. The skin 112 can be made from rigid or flexible materials depending on the testing need, whether or not configured as biofidelic.

Figure 2:
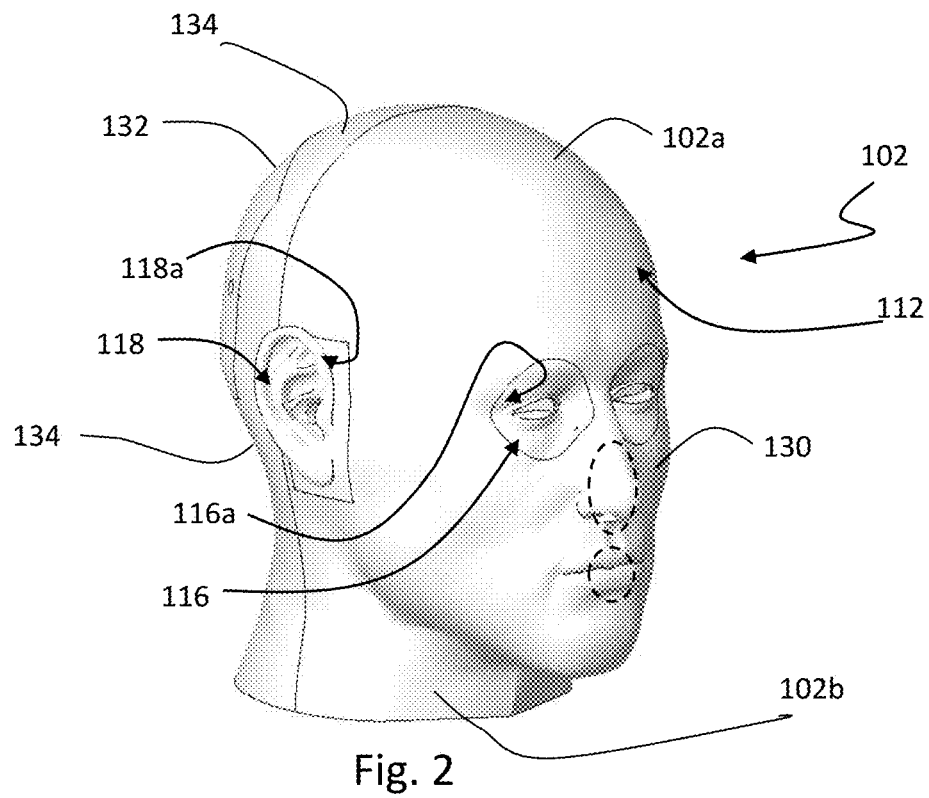
FIG. 2 shows an embodiment of a head assembly for a modular human surrogate.
Figure 4:
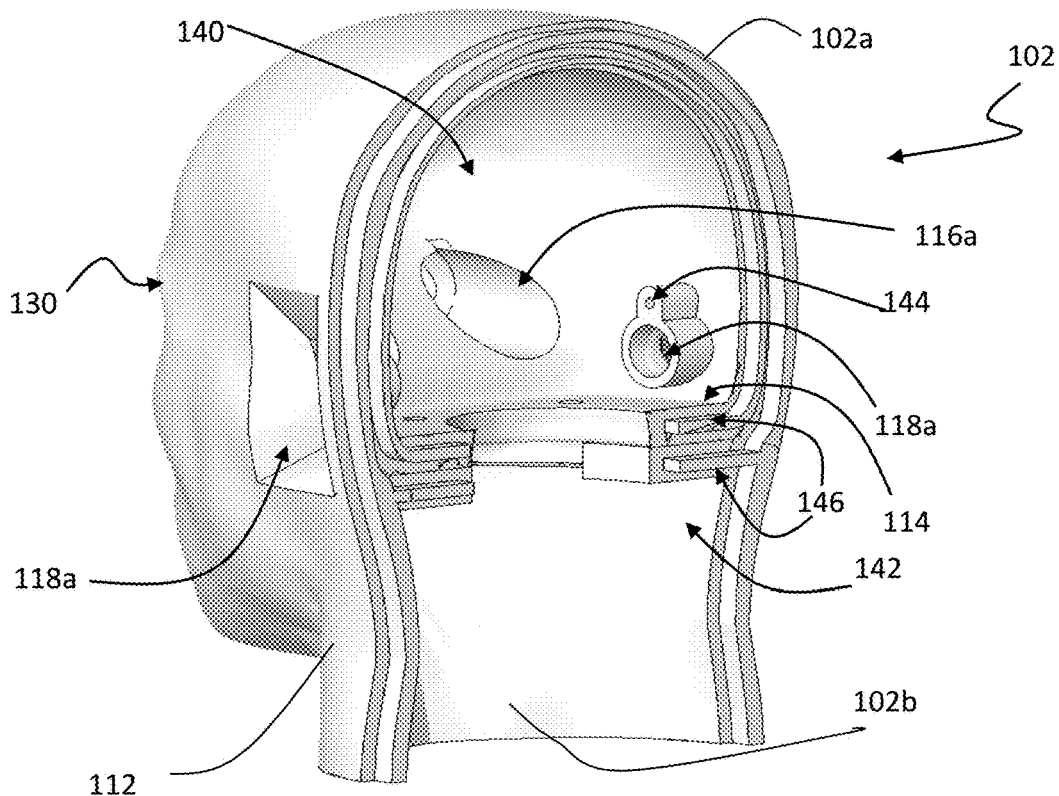
FIG. 4 shows an embodiment of a modular head showing the skin and skull integration with the open interior space.
Figure 5:
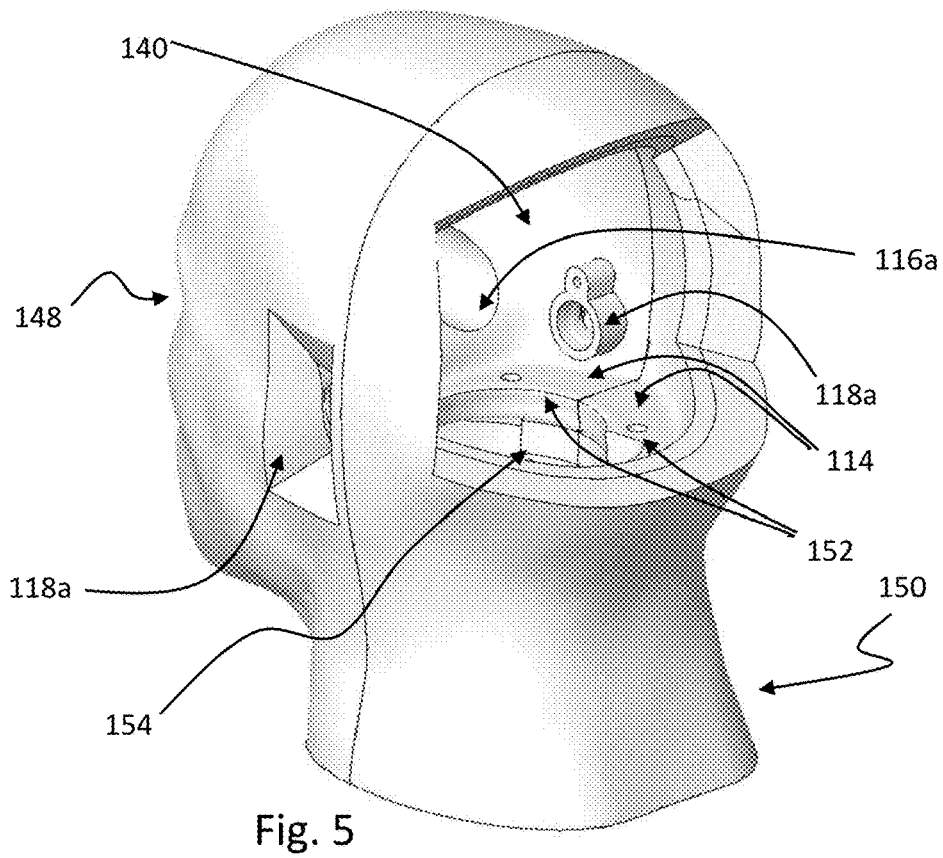
FIG. 5 shows an embodiment of a modular head showing the access panel being removed to access the open interior space.

FIG. 2 shows an example of the head module 102. The skin 112 of the head module 102 is shown to include dedicated ear ports 118a adapted to receive the ear modules 118, and to include dedicated eye ports 116a adapted to receive the eye modules 116. This can allow for easy installation and removal of the eye modules 116 and ear modules 118. The head module 102 includes a face 130 as a front portion separated from an openable head panel 132 by the back portion 134. The head panel 132 can access the internal parts of the head module 102, such as shown in FIGS. 4 and 5. The head panel 132 can open to reveal the instrumentation, which can communicate with the sensors of the anatomical modules (e.g., eye modules 116, ear modules 118). The anatomical modules can include electrical connectors that can operably couple with and connect to electrical connectors in the head module. In some aspects, the ear ports 118a and eye ports 116a can include mounting areas to fix the eye modules 116, ear modules 118 at the proper locations, which may also include fasteners (e.g., screws, bolts, etc.) to lock the modules within the ports.

Figure 3:
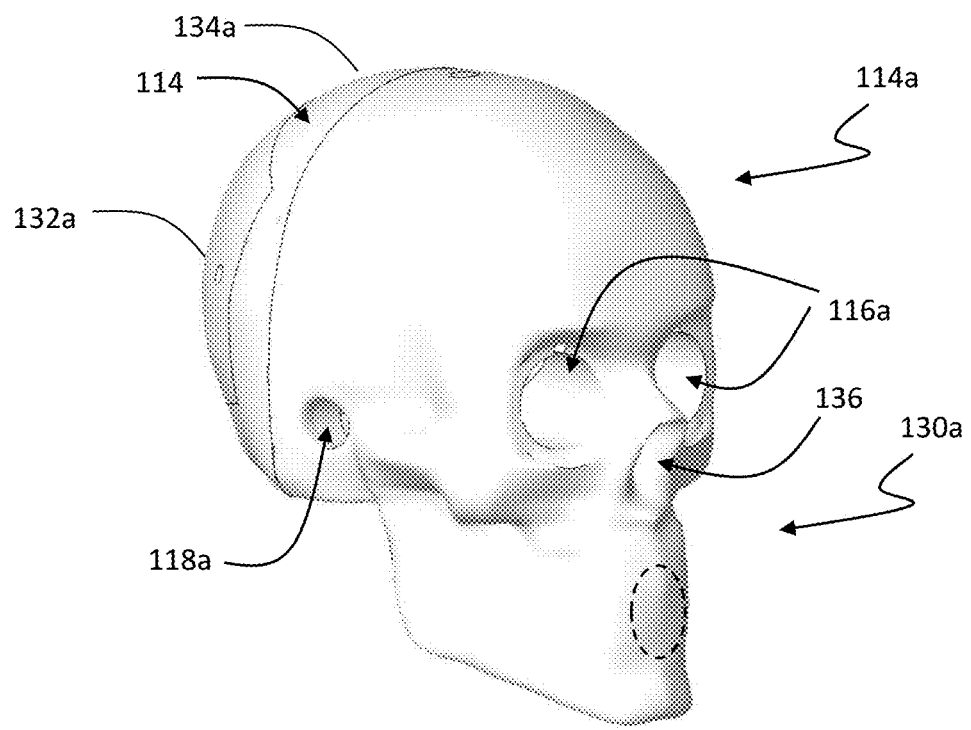
FIG. 3 shows an embodiment of a skull assembly for a modular human surrogate.

FIG. 3 shows an example of a skull 114a having the skull parts 114, which can be used with any head module 102. When comparing FIGS. 2 and 3, it is clear that the skull 114a has the ear ports 118a and eye ports 116a consistent with the skin 112 to allow for removable and exchangeable eye modules 116 and ear modules 118. The skull 114a has built in mounting areas located at the ear ports 118a and eye ports 116a to allow for the removable eye modules 116 and ear modules 118 to be secured to the skull, such as with a fastener. Also, the skull 114a is shown to have the skull face 130a as a front portion separated from an openable head panel 132a by the back portion 134a. Additionally, the skull 114a can include a nose port 136 that can be configured to receive a nose module (not shown) that may include sensors regarding smell (e.g., odor sensor) or other sensors. While not shown, a mouth port and corresponding mouth module may also be included (See dashed lines in FIGS. 2 and 3).

FIG. 4 shows the head module 102 having the internal chamber 140, which is defined by the skull parts 114 and neck parts 142. The ear ports 118a and eye ports 116a are also shown connecting with the internal chamber 140, where the fastener receiving holes 144 are also shown. FIG. 4 also shows that the skin 112 is modular and each part fits over the skull parts 114, which are shown in FIG. 3. The front and back skin 112 and skull parts 114 are joined with alignment guides 146 shown at the edges and rear of the skin 112 and skull parts 114 in FIG. 4. The alignment guides 146 can include slots in the skull parts 114 for receiving portions of the skin 112 as shown in order to facilitate alignment of the skin 112 with the skull parts 114. The front and back skin/skull assemblies can then be secured to each other using any fastener or adhesive creating an integrated full head for the test surrogate shown in FIG. 2 and FIG. 5. The modular head 102 may then be tested in isolation from the neck module or torso module based on NLW/NLE to be evaluated, or combined with the neck module and torso module as needed or desired.

Figure 11:
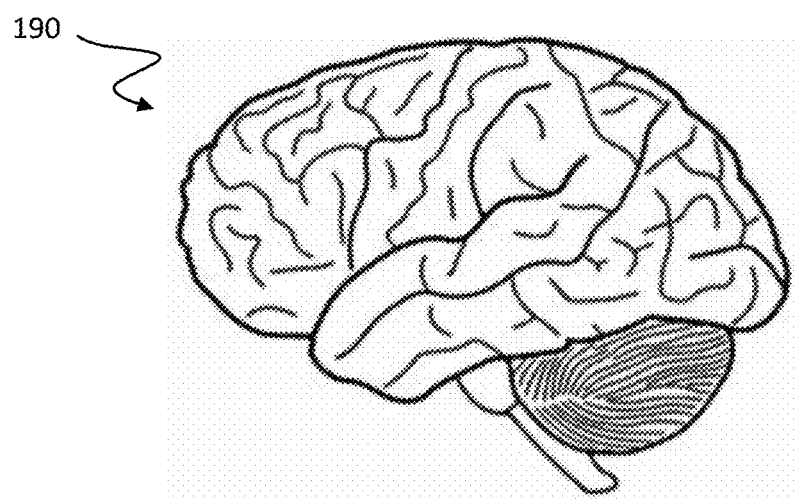
FIG. 11 shows an embodiment of a modular organ, shown as a modular brain.

FIG. 5 shows the front skin/skull assembly 148 coupled to the back skin/skull assembly 150 with the head panel 132 being opened to show the internal chamber 140. FIG. 11 shows a brain module 190 which can be outfitted with various sensors to monitor a brain response to stimuli exposure, such as pressure or blunt impacts, and that can be located in the internal chamber 140. FIG. 5 also shows that skin 112 and skull 114*a* have a removable access panel referred to herein as the head panel 132 that can be removed to allow access to instrumentation after the front skin/skull assembly 148 is coupled to the back skin/skull assembly 150 and closed and secured. The head panel 132 being removable allows for ease of use of the head module 102 as well as for allowing the wiring for instrumentation to be within the internal chamber 140 rather than being external to the test surrogate, where being external is unfavorable by possibly being influenced by exposure and response to stimuli. The base of the skull parts 114 also has mounting areas 152 to secure a neck attachment 154 to allow for head movement or to affix to a straight fixed neck support.

Figure 6:
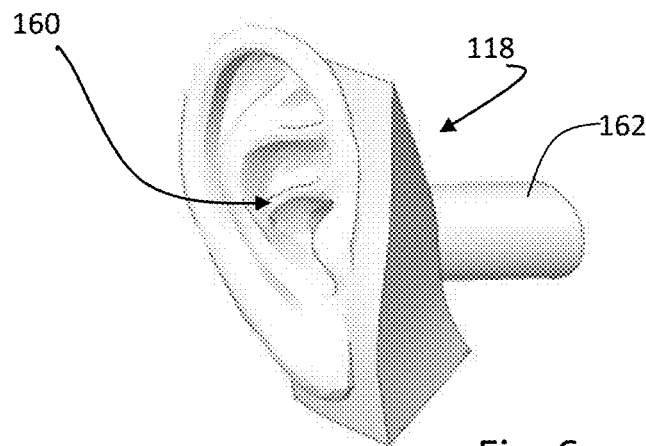
FIG. 6 shows an embodiment of a modular ear for use with a modular head of a modular human surrogate.

FIG. 6 shows a removable ear module 118 that can be used with a MSMS 100, shown with the full anatomical outer ear body 160 and ear canal body 162 formed as a cylinder. The ear canal body 162 can be formed to terminate at the tympanic membrane, which is the first point of failure during noise induced hearing issues. Accordingly, the sound sensors or other sensors (e.g., pressure) can be mounted in the ear canal body 162 and/or at the terminal thereof so as to simulate the tympanic membrane. The sensors or other instrumentation for the ear module 118 can be placed at specific locations so that the sensors are properly placed when the removable ear module 118 is secured to the skull parts 114 inside the head module 102. Optionally, instrumentation can be placed through the ear canal body 162 to be located at the surface of the outer ear body 160 if the ear canal in the ear canal body 162 is not desired during evaluation of the stimuli exposure. The ear canal body 162 can be adapted to slidably fit into the ear ports 118*a*, which may be retained therein by friction or a fastener. Similarly, the outer ear body 160 can fit into a corresponding cutout or recess in the skin.

Figures 7, 7A:
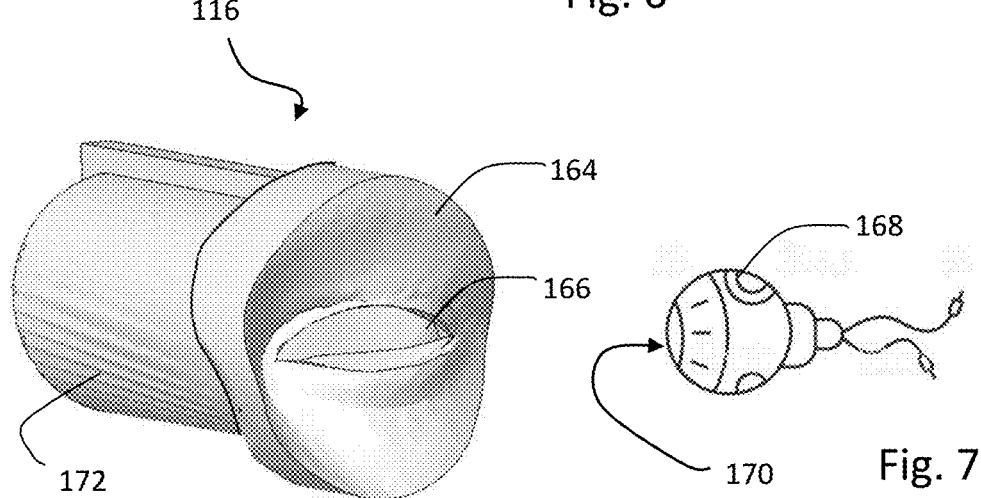
FIG. 7 shows an embodiment of a modular eye for use with a modular head of a modular human surrogate.
FIG. 7A shows an embodiment of a modular eyeball for use with a modular eye and modular head of a modular human surrogate.

FIG. 7 shows a removable eye module 116 that can be used with the head module 102 of the MSMS 100. As shown, the eye module 116 can include an anatomical outer eye body 164 having an eyeball cavity 166. The eyeball cavity 166 can receive optical sensors or other types of sensors. As shown in FIG. 7A, a surrogate modular eyeball 168 can be adapted as a device or as a lens 170 or covering (without components or sensors) for the eyeball cavity 166 through which light stimuli can pass. The surrogate modular eyeball 168 can be helpful because the curvature of the eye can influence the human response to light and other stimuli. As such, the eye module 116 includes an eye module stem 172 extending from the outer eye body 164, and which can be included in the eyeball cavity 166, and which can provide area for sensors or other instrumentation while remaining anatomically accurate.

Figure 8:
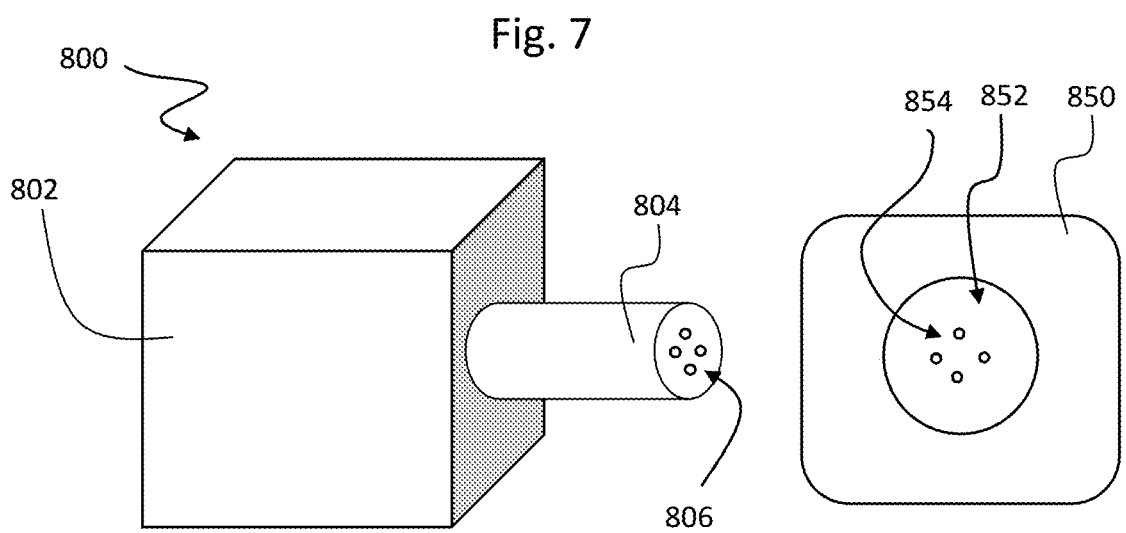
FIG. 8 shows an embodiment of an anatomical module for use with a modular human surrogate.
Figure 8A:
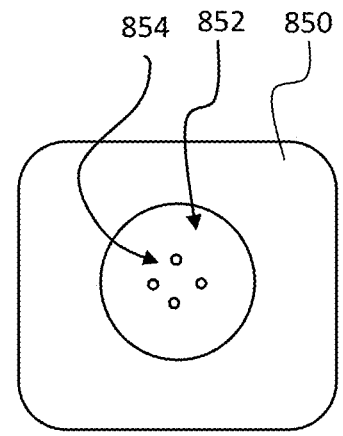
FIG. 8A shows an embodiment of a portion of a surrogate including a port for receiving and electrically connecting with an anatomical module.

FIG. 8 includes a schematic representation of an anatomical module 800 that can be configured with an outer portion 802 that includes anatomical features of a body part, such as the eye module 116 or ear module 118 as described herein, or of a mouth module, nose module, or any other anatomical body part. The anatomical module 800 can include a stem portion 804 connected to a back part of the outer portion 802, where the stem portion 804 is adapted to be received into a port (e.g., eye port 116*a* or ear port 118*a*) of the MSMS 100. As shown, the stem portion 804 can include electrical connectors 806, which can be used to electrically connect the sensors or other instrumentation in the anatomical module 800 with the main instrumentation of the MSMS, such as a computer system. Accordingly, FIG. 8A shows a body module 850 into which an anatomical module 800 fits into a conduit 852 adapted to slidably receive the stem portion 804, which can be friction fit or coupled with a fastener. The conduit 852 can include electrical connectors 854 that can electrically couple with the electrical connectors 806 of the stem portion 804 when received therein.

Figure 9:
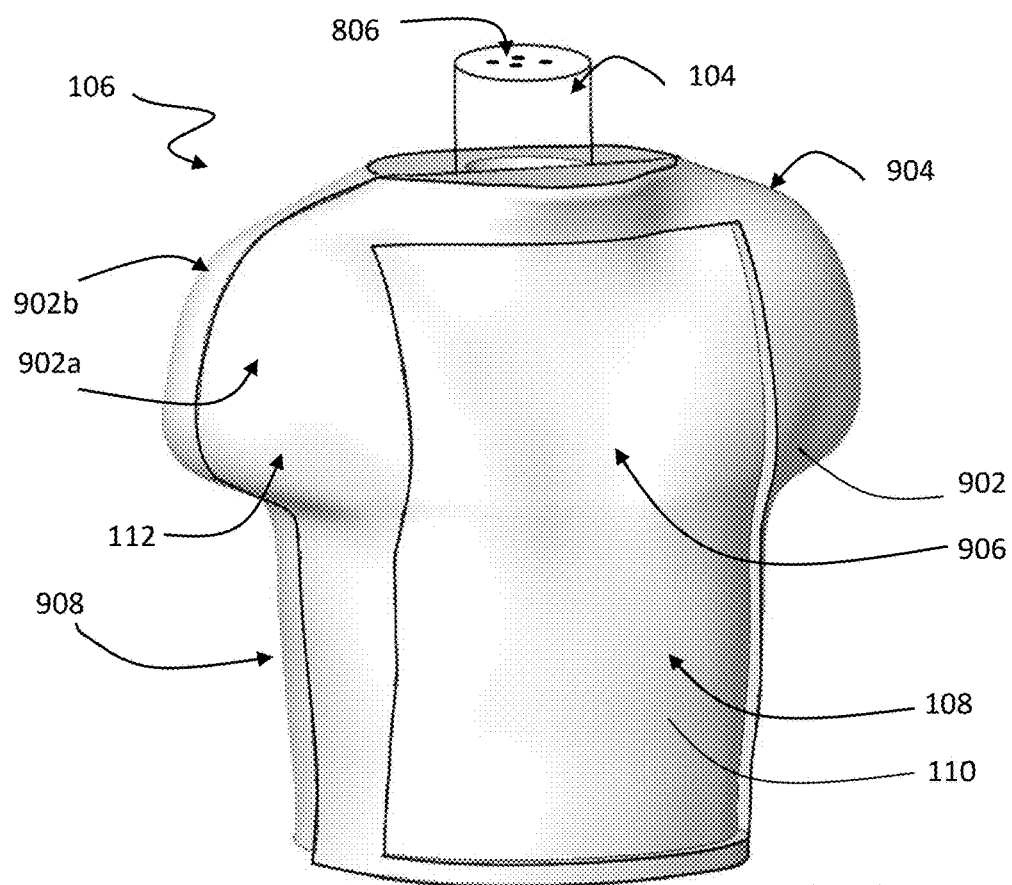
FIG. 9 shows an embodiment of a modular torso with a neck stem for receiving a modular head of a modular human surrogate.

FIG. 9 shows a torso module 106 having the neck stem 104 extending from an anatomical torso body 902. The neck stem 104 may be configured to receive a head module 102 thereon, and thereby may include electrical connectors 806 that electrically connect to the head module 102, similarly as shown in FIGS. 8-8A. The torso body 902 is anatomically accurate with shoulders 904 and a curved chest 906 and back 908. The torso body 902 can be prepared by coupling a front torso body portion 902*a* with a back torso body portion 902*b*. While shaped as a male, the torso body 902 may be shaped as a female, child or the like. The anatomical torso body 902 is shaped to allow for clothing, battle armor, or other realistic garments to be put on torso module 106 to mimic realistic conditions. The torso module 106 can have a rigid composition, a flexible skin 112, or any combination depending on the NLW/NLE stimuli exposure under evaluation. The modular torso 106 also allows for sensors and other instrumentation to be populated along the surface of the torso body 902 as well as inside an internal compartment 108 under the chest plate 110. The modular torso 106 can be configured with one or multiple impact sensors (e.g., impact pads), which can be fit under the skin, such as by being in the chest plate 110, or other location depending on the NLW/NLE stimuli exposure under evaluation.

Figure 10:
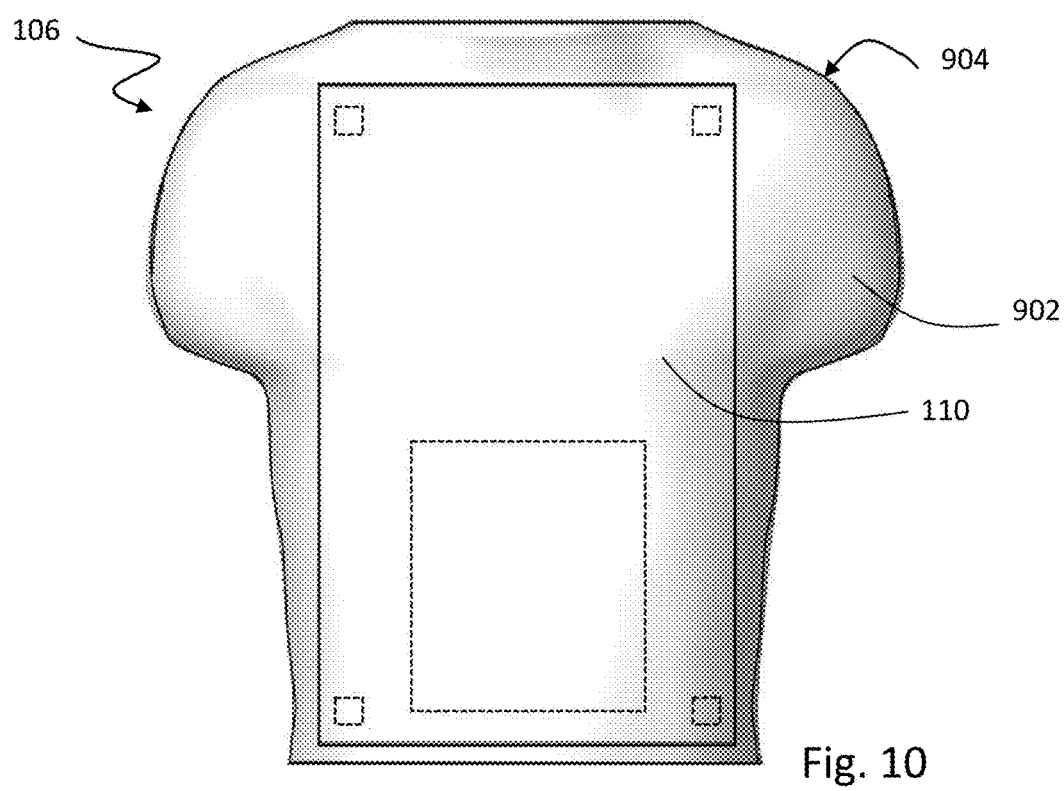
FIG. 10 shows an embodiment of a modular torso having a removable chest plate, which can have various configurations.

In FIG. 10, the torso module 106 is shown with a singular chest plate 110 configuration that is removable from the front of the torso body 902. This chest plate 110 can include a conductive outer layer and enclosed circuitry that mimics the electrical resistance and conductivity of the human body. The dashed lines forming the corner squares can identify fastener locations for the chest plate 110 and torso body 902. The larger dashed line rectangle can show a location of an internal compartment 108. The chest plate 110 can be configured with electrical sensors so that the torso module 106 can be used for testing EMD stimuli, in order to obtain accurate data to simulate the consequences a human body can experience as a response to EMD stimuli NLW/NLE. In some aspects, the chest plate 110 can be configured for measuring blunt force impact and/or EMD electrical pulses, and thereby include the appropriate sensor packages. It should be recognized that the chest plate 110 can have an outer skin layer as well as a body layer that fits onto the torso, where the body layer of the chest plate 110 can be considered to be a stem and the hole in the torso that receives the chest plate being a port that receives the stem of the chest plate 110. Here, the stem fits into a port where any cross-sectional profile, shape or size (e.g., width or length) can be used for both the stem and port. As such, the chest plate 110 can be adapted as an anatomical module such as in FIG. 8 and the torso module can be adapted with the opening to the internal chamber being configured as the conduit 852 of FIG. 8A.

In any embodiment, the skin of a module can be configured as a biofidelic outer layer that mimics the human skin. Such skin of the modular surrogate can be made from rigid or flexible materials based on NLW/NLE evaluation need.

Similar to the surrogate brain having the sensors and other instrumentation to fit within the head module, a surrogate organ to simulate any type of organ can be prepared to be anatomically correct and to have sensors and other instrumentation therein. As such, any organ in the torso, such as heart, lungs, stomach, intestines, or other, may be used for preparing an anatomically correct surrogate configured as a removable module with the sensors and other instrumentation in order to provide stimuli data to the computing system (e.g., controller).

While the figures illustrate a human shaped MSMS, the shape may be of any animal, which animal shapes are incorporated herein by specific reference. The animal shapes can be anatomically correct, and may include the ports and anatomical modules with sensors as described herein.

In some embodiments, the modular human surrogate and test platform can be used to generate realistic human response data via anatomically correct features and sensor locations when exposed to non-lethal weapons (NLW) and non-lethal exposures (NLE), where the term NLE can include NLW as a subset thereof. As shown, the modular human surrogate can include an anatomical modular head with a hard skull material to simulate bone and softer or flexible skin surrogate to simulate realistic skin, which can be biofidelic. The modular human surrogate can include an anatomical modular torso that can receive the module head. A supportive neck, such as a neck stem, can be used to couple the head to the torso so as to be rotatable or fixed relative to each other. The modular human surrogate can include one or more anatomic modules that simulate the shape and sensory function of an anatomical body part, such as ear modules shaped as ears with sound sensors, pressure sensors, or other, or eye modules shaped as the surrounding of an eye with an eyeball surrogate with optical or other light sensors. In some aspects, each anatomical module can include at least one sensor or sensor package. In other aspects, an inactive anatomical module may be devoid of a sensor. The modular human surrogate can include a data recording system, such as a computer, that allows for collection, storage, and transmission of the stimuli data obtained during the NLW/NLE evaluation. The data recording system can be communicatively coupled with sensors or other instrumentation of the anatomical modules, such as through the electrical connectors, wires, or the like as well as optical communication components (e.g., fiber optics and light emitters and receivers) or wireless communication components (e.g., Bluetooth WiFi, or other).

In some embodiments, the head module can include skull bones, which can be made from rigid materials ranging from wood, plastics, ceramics or composites. Some examples of rigid materials can include hard polyurethanes, acrylonitrile butadiene styrene (ABS), hydroxyapatite, or others.

In some embodiments, the skin of the surrogate can be prepared to be skin-like, and made from a flexible material (e.g. flexible polyurethane, silicone, etc.). However, the skin may be hard, such as plastic.

In some embodiments, a head module can include ports for receiving the various anatomical modules, such as ear module, eye module, nose module, or mouth module. Accordingly, the internal structural skull and skin outer layer can have the ports configured as mounting areas for the removable anatomical modules.

In some embodiments, the anatomical modules can include outer and/or inner anatomical shapes. For example, the removable eye modules can be shaped as an outer eye area with surrounding skin along with an eye socket, and may include a surrogate eyeball. The anatomical shape can include the realistic eye socket that can be populated with both sensors and/or materials meant to mimic the composition of the eye, such as with a surrogate eyeball.

Also, the removable ear modules can be anatomical in shape, and can include a full ear canal terminating at the location of the tympanic membrane as well as realistic pinnae and lobes on the outside. Additionally, the removable ear modules allow for sensors or other instrumentation at the tympanic membrane, along the ear canal, or at the ear canal entrance as well as any location.

In some embodiments, the skull and skin of the head module can be designed with a head panel that can be removed to access an internal chamber. The internal chamber area can be used for a wiring harness and instrumentation wiring access as well as provide for connections between the anatomical modules and the computing system. The head panel can be anatomically shaped and may be removed and attached via fasteners, such as screws, bolts, quick release, snap-couplings or the like.

In some embodiments, the skull and skin of the head module can have attachment features at the base of the skull and skin parts to allow for attachment to a neck portion, such as the neck stem. The neck attachment features can be any type of fasteners, or the neck stem can be threaded with the neck of the head module having a corresponding threading. The mounting of the head module to the neck attachment can be affixed to a flexible or rotatable (e.g., realistic) neck surrogate or a fixed (e.g., stiff) neck surrogate. One example is the HybridIII flexible neck dummy as in U.S. Pat. No. 9,972,220, which is incorporated herein.

In some embodiments, the modular human surrogate can include an anatomical torso. The anatomical torso can be attached to a neck for a head/neck/torso combined test platform. Alternatively, the head module may be integrated with a modular torso via an integrating neck. The torso can also be configured to be anatomically correct. The anatomical torso can include mounting areas on the outer surface and/or inside the torso for sensors and other instrumentation tailored to the type of NLW/NLE to be evaluated. The sensors and other instrumentation can be modular so as to be replaceable so a standard surrogate can be configured with specific combination of sensor packages to sense one or a combination of stimuli exposures. The anatomical torso can be composed of rigid structural elements (e.g. Acrylonitrile butadiene styrene, ABS) on the inside and/or flexible material (e.g. polyurethane, silicone) for skin or other flexible structural elements, or any combination of these materials meant to provide a realistic human surrogate.

In an example, the torso module can be made from a rigid ABS plastic shell, which contains an electrical circuit platform and components, and can have an outer layer of a conductive outer material (e.g. flexible polyurethane foam, flexible polyurethane plastic, silicone) meant to replicate the human electrical conductivity response to EMD type NLE stimuli. In some aspects, the sensor system can include electrically conducting barbs adapted to respond to EMD stimuli, which barbs can penetrate the conductive layer of the torso (e.g., skin) to capture an electrical discharge event of the EMD stimuli and subsequent simulated human response via the sensors.

The surrogates described herein (e.g., MSMS) can be configured for use in testing any NLE event, whether by NLW, contaminate release (e.g., biological, nuclear radiation, etc.), recording stimuli data with one or more sensors, and processing (e.g., recording, saving, analyzing, transmitting, or other) the stimuli data with a computing system in the surrogate. Such a method can be performed using any combination of the above anatomical modules and surrogate configurations in order to capture stimuli data and measure simulated human responses from the sensors from a NLE event. Such an NLE event may or may not be from a NLW system. The NLE event may include one or more of the following stimuli: sound, light (e.g., broadband and laser), heat (e.g., laser or RF, etc.), blunt impact, pressure, and electro muscular stimulation (e.g., EMD), or others.

In some embodiments, the MSMS described herein can help development of suitable NLW or NLE for different uses in order to measure and record the stimuli as received by a subject. The NLW or NLE can be altered by iterations to obtain something that is capable of incapacitating targeted personnel or material immediately, while minimizing fatalities, permanent injury to personnel, and undesired damage to property in the target area or environment. Some examples of NLW include: stun grenades (e.g., M84), lasers (e.g., green laser), directed energy weapons (e.g., active denial systems (ADS 1), long range acoustic devices (e.g., LRAD 1000×), distributed sound and light array (e.g., DSLA), electrical discharge devices (e.g., EMD, X26 TASER), modular crowd control munition, impact projectiles (e.g., 12 GA Blunt Impact) or rubber bullets, launchable EMD (e.g., 40 mm HEMI) or others. As such, the sensors or sensor packages can be configured to measure the stimuli from one or more NLE events.

In some embodiments, an acoustic sensor can sense sound (dB), a blast sensor can detect pressure over time, a light sensor can detect intensity ($W/cm^2$), a blunt impact sensor can detect loading (e.g., force), EMD (e.g., taser) can detect voltage, PRR, current, charge, etc., laser or RF heating sensors can detect temperature.

In some embodiments, the computing system of the surrogate (MSMS) can include software for performing calculations with computer models that predict the risk of significant injury to human targets of the NLE stimuli. The software can also include collection of detailed models that provide predictions for a range of human effects and permits a standardized and centralized approach for non-lethal weapon human effects assessments, which can be processed with the stimuli data collected as described herein.

The software includes the capability to assess injury potential from blunt trauma, thermal injury, blasts and acoustic stimuli, visual effects of broadband optical stimuli, radio-frequency directed energy, thermal laser effects, electro-muscular disruption, underwater acoustic effects, mild traumatic brain injury, and behavioral response effects as well as many others.

The computing system of the surrogate can be used to process computer models in order to allow NLE/NLW developers to evaluate the effectiveness of stimuli against the risk of significant injury. As part of that process, researchers can use the surrogate (MSMS) to measure, validate, verify and accredit the various implemented models for stimuli. Accordingly, the surrogate can be used in methods to gather experimental stimuli input data that can be used for comparison to those models, gain meaningful human response data from NLE events, and provide a testing platform with realistic and relevant human features with sensors that can gather multiple NLE events concurrently. The human-like features of the testing surrogate can be used to accurately represent certain exposure levels. Additionally, surrogate models can be used to assess effects of clothing and other artifacts associated with the surrogate, and can be used in complex operational scenarios.

In some embodiments, blunt impact assessments may require computation models that are easy to propagate and can quickly assess sensitivity to material property values and projectile ballistic changes, in addition to a high fidelity test surrogate as provided herein that is capable of measuring the various exposures and validating the computational models. This dynamic interplay between mechanical and computational models that can be performed with the MSMS described herein can provide researchers and developers of NLE with an opportunity to characterize and influence the design of such exposures. Modularity of the surrogate can be beneficial due to the wide variety of stimuli to be evaluated in different NLE. The modular human surrogate can be paired with a portable data collection system, which can be placed in a testing environment and monitored remotely as needed. As such, the sensors or computing system of the MSMS can transmit the stimuli data to such data collection systems, or such data collection systems can be included in the computing system of the MSMS.

In some embodiments, the anatomical modular head can be designed for a common or average anatomy (e.g., 50th percentile male geometry) and modified to become modular in nature. For example, the eyes and ears can be made modular so they can be easily removed or exchanged. This allows replacement of a module with a broken sensor or change the eye or ear sensor hardware for a different stimuli testing. The anatomical head module can include an outer layer of silicone material, which represents the skin on a human head. The inner layer of the anatomical head can be the skull pieces made of a harder polyurethane material. Both layers are secured together after being produced from molds, which improves the integrity and ruggedness of the finalized head module for the surrogate. An access panel in the back of the head can allow access to instrumentation before, during, and after testing and ease of switching out sensors based on need to measure a certain stimulus or stimuli. The eyes and ears can be made from the same silicone materials as the outer skin of the anatomical head module. Fasteners inside the skull allow for the ears and eyes modules to be secured to the head module, which are electrically connected when in place. The modular ears allow for two configurations, such as one with acoustic or pressure sensors mounted at the tympanic membrane area and one for sensors mounted at the entrance to the ear canal, or both. The anatomical ear canal can be configured to act as a natural amplifier similar to the function of a real ear canal.

The MSMS can include a fixed neck module or flexible neck module depending on whether head movement/acceleration needs to be measured. For example, using a laser dazzling NLW does not require measuring head movement, so a fixed neck would be ideal for that particular testing. For a flashbang grenade which has pressure, light, and sound components, the head movement in response to the pressure component needs a flexible (and realistic) neck. The modular surrogate supports a flexible Hybrid III neck using a 6 degrees of freedom (DOF) or other sensor suite to measure head movement.

The torso module can be provided in various configurations, or as a single torso body with removable chest plates and/or back plates that have specific types of sensor packages, or combinations of both.

A first embodiment of a torso module is configured to be capable of switching out pressure sensors and accelerometers to measure the blunt impact forces on the front of the chest, such as with the exchangeable chest plates. This configuration has an array of sensors suspended in a blend of materials that can be changed based on testing focus. For example, if higher blunt impact loadings are expected, the sensor suite (e.g., in chest panel) can easily be switched, but still utilize the same form factor. The outer layer of this torso has a realistic skin type material.

A second torso embodiment can be designed for evaluating electro-muscular disruption (EMD) type NLW. This torso module has the same form factor as the first torso in order to maintain consistency across the geometries of the NLW surrogate. The second embodiment uses an acrylonitrile butadiene styrene (ABS) 3-D printed back and partial front structure. The front of the torso has a modular and removable single or multi-pad design with a conductive foam outer layer. An EMD NLW, such as a Taser®, uses barbs that discharge a voltage, which incapacitates a human target. The EMD measuring torso on the NLW surrogate has roughly the same resistance as the human body (e.g., 600 Ohm) and can return important metrics, such as peak voltage, net charge, pulse repetition rate, pulse duration, or the like. The torso can also utilize realistic skin type materials.

In some embodiments, a modular surrogate can include: a body having an external body surface with an anatomical shape, wherein the body includes an internal chamber with at least one port formed in the body extending inwardly from the external body surface; at least one anatomical module having an external module portion and a module stem coupled to the external module portion, the module stem being configured to be received into a corresponding module port of the at least one port, the external module portion having an external module surface with an anatomical shape, when the module stem is located in the module port, the external body surface matches with the external module surface to provide a continuous anatomical shape; at least one sensor located in the at least one anatomical module; and at least one controller, wherein when the at least one anatomical module is coupled with the body, the at least one sensor is capable of being operably coupled with the at least one controller. In some aspects, the body has an anatomical shape of at least one of a head or a torso. In some aspects, the body has an anatomical shape of a head and is configured as a head module, the modular surrogate further comprising a second body having an anatomical shape of a torso configured as a torso module. In some aspects, the body has an anatomical shape of a torso and is configured as a torso module, the modular surrogate further comprising a second body having an anatomical shape of a head configured as a head module.

In some embodiments, the modular surrogate can include a neck stem configured to be coupled with the head module and torso module so as to link the head module with the torso module. In some aspects, the at least one anatomical module is configured as at least one of: an eye module; an ear module; a nose module; a mouth module; or a chest plate module. In some aspects, the anatomical shape is a human anatomical shape. In some aspects, the anatomical shape is a non-human animal anatomical shape. In some aspects, the at least one anatomical module includes a plurality of sensors.

In some embodiments, the at least one controller includes a processor and a memory device having instructions that when executed by the processor causes collection of stimuli data from the at least one sensor. In some aspects, the instructions cause the processor to save the stimuli data on a data memory device. In some aspects, the instructions cause the processor to transmit the stimuli data to an external computing system. In some aspects, the at least one sensor is operably coupled with the at least one controller. In some aspects, the at least one anatomical module is electrically coupled with the at least one controller or optically coupled with the at least one controller or wirelessly coupled with the at least one controller. In some aspects, the at least one anatomical module includes an electrical connector that electrically connects with an electrical connector of the at least one controller. In some aspects, the at least one controller is configured to record stimuli data from the at least one sensor in real time. In some aspects, the at least one controller is configured to correlate stimuli data from the at least one sensor with a real human response to the stimuli input into the sensor that causes formation of the stimuli data.

In some embodiments, each anatomical module includes a first sensor for measuring a first type of stimuli and a second sensor for measuring a second type of stimuli, wherein the first type of stimuli is different from the second type of stimuli. In some aspects, the at least one sensor is selected from a pressure sensor, sound sensor, light sensor, electrical sensor, temperature sensor, or blunt force sensor, or combination thereof.

In some embodiments, the external body surface and/or external module surface includes a surrogate skin layer. In some aspects, the external body surface and/or external module surface includes a surrogate skin layer that is biofidelic. In some aspects, the at least one anatomical module includes a head module having a skull assembly covered by a skin surrogate layer. In some aspects, the head module includes alignment guides in the skull assembly for receiving and aligning the skin surrogate layer.

In some embodiments, the modular surrogate can be configured as a kit and can includes a plurality of anatomical modules for each type of anatomical module, each of the plurality of anatomical modules including a sensor package with one or more sensors, wherein each sensor package is different for different anatomical modules for the type of anatomical module. In some aspects, a plurality of right ear modules are provided. In some aspects, a plurality of left ear modules are provided. In some aspects, a plurality of right eye modules are provided. In some aspects, a plurality of left eye modules are provided. In some aspects, a plurality of chest plate modules are provided. In some aspects, the modules of a certain anatomical type each have different sensor packages of one or more sensors compared to the others of the certain anatomical type.

In some embodiments, a modular surrogate can include: a head module having a head body having an external body surface with an anatomical shape of a head, wherein the head body includes an internal chamber with at least one eye port and at least one ear port formed in the body extending inwardly from the external body surface; at least one eye module having an external eye portion and a module stem coupled to the external eye portion, the module stem being configured to be received into a corresponding eye port of the at least one eye port, the external eye portion having an external eye surface with an eye shape, when the module stem is located in the module port, the external eye surface matches with the external module surface to provide a continuous anatomical shape; at least one ear module having an external ear portion and a module stem coupled to the external ear portion, the module stem being configured to be received into a corresponding ear port of the at least one ear port, the external ear portion having an external ear surface with an ear shape, when the module stem is located in the module port, the external ear surface matches with the external module surface to provide a continuous anatomical shape; a torso module configured to be linked to the head module; at least one sensor located in the at least one eye module; at least one sensor located in the at least one ear module; at least one sensor located in the torso module; and at least one controller, wherein: when the at least one eye module is coupled with the head module, the at least one sensor in the at least one eye module is capable of being operably coupled with the at least one controller; when the at least one ear module is coupled with the head module, the at least one sensor in the at least one ear module is capable of being operably coupled with the at least one controller; and when the at least one sensor in the torso module is capable of being operably coupled with the at least one controller.

In some embodiments, a method of testing exposure to a stimulus can include: providing a modular surrogate of one of the embodiments; exposing the modular surrogate to at least one stimulus; measuring the at least one stimulus with the at least one sensor to obtain stimulus data; and recording the stimulus data with the controller. In some aspects, the method can include: determining the at least one stimulus; and preparing the modular surrogate such that the at least one sensor measures the at least one stimulus. In some aspects, the method can include the at least one stimulus being at least one of: sound, light, heat, blunt impact, pressure, or electro-muscular stimulation.

In some embodiments, the method can include: exposing the modular surrogate to a plurality of stimuli; measuring the plurality of stimuli with a plurality of sensors to obtain stimuli data; and recording the stimuli data with the controller. In some aspects, the method can include dressing the modular surrogate with clothing and/or protective equipment. In some aspects, the method can include recording the stimulus data in real time. In some aspects, the method can include correlating the stimulus data with a living human response to the at least one stimulus.

In some embodiments, the method can include: determining a first sensor to be malfunctioning; and replacing the malfunctioning first sensor with a functional first sensor. In some aspects, the method can include: determining a first sensor in a first anatomical module to be malfunctioning; and replacing the malfunctioning first anatomical module with a functional first anatomical module. In some aspects, the method can include removing a first anatomical module with a first sensor package from a first port of the modular surrogate, and installing a second anatomical module with a second sensor package in the first port of the modular surrogate.

In some embodiments, the method can include transmitting the stimulus data from the controller to an external computing system. In some aspects, the method can include storing the stimulus data on a storage medium of the controller. In some aspects, the method can include setting the modular surrogate to measure the at least one stimulus.

In some embodiments, a method of developing a non-lethal exposure with a modular surrogate can include: determining the at least one stimulus of the non-lethal exposure configuring the modular surrogate with at least one sensor for measuring the at least one stimulus; and performing the method steps of one of the embodiments.

In some embodiments, a method of developing a non-lethal weapon with a modular surrogate can include: determining the at least one stimulus of the non-lethal weapon; configuring the modular surrogate with at least one sensor for measuring the at least one stimulus; and performing the method steps of one of the embodiments.

As used herein, the term "stimuli" can refer to one stimulus or a plurality of stimuli.

EXAMPLES

The MSMS as described herein was used in different modular configurations to test different stimuli exposures. The data provided in Table 1 shows that the MSMS is effective by comparing the measured data with the specifications of the NLE.

TABLE 1

| Measured/Calculated Metric | NLW-Surrogate Results (CFDRC) | Specifications (M26 Taser) |
|---|---|---|
| Pulses per second (PPS) | 15.6 | 15 PPS (alkaline batteries) |
| Main Phase Duration | 10 μsec | 8.8 to 8.9 μsec |
| Entire Pulse Duration | 45 μsec | 32 to 60 μsec |
| Main Pulse Voltage | 12 kV | 9.4 to 9.7 kV |
| Pulse Charge | 71.2 μC +/− 6.3 μC | 70 to 120 μC |

The ocular sensor system was evaluated using two commercially available laser protective eyewear against a commercially available laser pointer. The testing results shown in Table 2 showed that both sets of laser eyewear had similar performance for this exposure.

TABLE 2

| | Without Eyewear (Peak Intensity in W/cm$^2$) | With Honeywell Eyewear (Peak Intensity in W/cm$^2$) | With NoIR Eye wear (Peak Intensity in W/cm$^2$) |
|---|---|---|---|
| Average | 0.001075 | 0.000184 | 0.000192 |
| Percent Different | 0 | 83% | 82% |

A use case test was conducted for multiple sensors to capture data concurrently as might be necessary in collecting data from a NLW such as a flashbang. These types of NLW output broadband light, loud sound, and blast overpressure. A pyrotechnic commonly used for entertainment, and outputs was used to simulate a flashbang NLW. The NLW surrogate head was outfitted with the eye sensor, pressure sensor in the eye and one ear, and a sound sensor in the opposite ear. All sensors were sampled at the same time during the test. The results are shown in Table 3. All sensors and data collection function within expected ranges.

TABLE 3

| Test Number | Peak Sound Level (dB) | Pressure (psi) |
|---|---|---|
| Test 1 (70 inch offset) | 141 | 0.4 |
| Test 2 (70 inch offset) | 138 | 0.38 |
| Test 3 (36 inch offset) | 158 | 0.9 |

For processes and methods disclosed herein, the operations performed in the processes and methods may be implemented in differing order. Furthermore, the outlined operations are only provided as examples, and some operations may be optional, combined into fewer operations, eliminated, supplemented with further operations, or expanded into additional operations, without detracting from the essence of the disclosed embodiments.

The present disclosure is not to be limited in terms of the particular embodiments described in this application, which are intended as illustrations of various aspects. Many modifications and variations can be made without departing from its spirit and scope. Functionally equivalent methods and apparatuses within the scope of the disclosure, in addition to those enumerated herein, are possible from the foregoing descriptions. Such modifications and variations are intended to fall within the scope of the appended claims. The present disclosure is to be limited only by the terms of the appended claims, along with the full scope of equivalents to which such claims are entitled. The terminology used herein is for the purpose of describing particular embodiments only, and is not intended to be limiting.

In one embodiment, the present methods can include aspects performed on a computing system. As such, the computing system can include a memory device that has the computer-executable instructions for performing the methods. The computer-executable instructions can be part of a computer program product that includes one or more algorithms for performing any of the methods of any of the claims.

In one embodiment, any of the operations, processes, or methods, described herein can be performed or cause to be performed in response to execution of computer-readable instructions stored on a computer-readable medium and executable by one or more processors. The computer-readable instructions can be executed by a processor of a wide range of computing systems from desktop computing systems, portable computing systems, tablet computing systems, hand-held computing systems, as well as network elements, and/or any other computing device. The computer readable medium is not transitory. The computer readable medium is a physical medium having the computer-readable instructions stored therein so as to be physically readable from the physical medium by the computer/processor.

There are various vehicles by which processes and/or systems and/or other technologies described herein can be effected (e.g., hardware, software, and/or firmware), and that the preferred vehicle may vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The various operations described herein can be implemented, individually and/or collectively, by a wide range of hardware, software, firmware, or virtually any combination thereof. In one embodiment, several portions of the subject matter described herein may be implemented via application specific integrated circuits (ASICs), field programmable gate arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware are possible in light of this disclosure. In addition, the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a physical signal bearing medium include, but are not limited to, the following: a recordable type medium such as a floppy disk, a hard disk drive (HDD), a compact disc (CD), a digital versatile disc (DVD), a digital tape, a computer memory, or any other physical medium that is not transitory or a transmission. Examples of physical media having computer-readable instructions omit transitory or transmission type media such as a digital and/or an analog communication medium (e.g., a fiber optic cable, a waveguide, a wired communication link, a wireless communication link, etc.).

It is common to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. A typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems, including feedback loops and control motors (e.g., feedback for sensing position and/or velocity; control motors for moving and/or adjusting components and/or quantities). A typical data processing system may be implemented utilizing any suitable commercially available components, such as those generally found in data computing/communication and/or network computing/communication systems.

The herein described subject matter sometimes illustrates different components contained within, or connected with, different other components. Such depicted architectures are merely exemplary, and that in fact, many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include, but are not limited to: physically mateable and/or physically interacting components and/or wirelessly interactable and/or wirelessly interacting components and/or logically interacting and/or logically interactable components.

Figure 12:
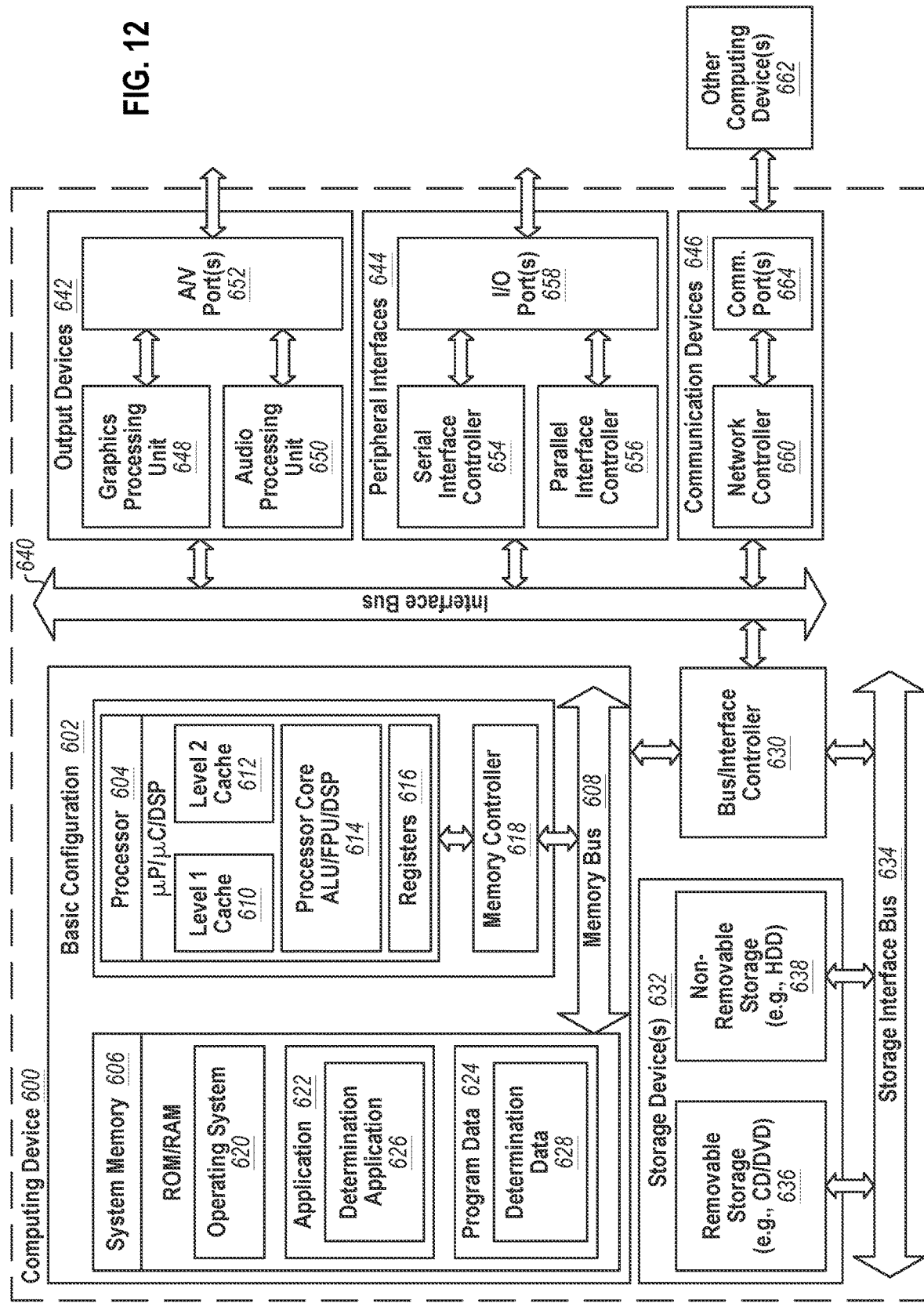
FIG. 12 shows an embodiment of a controller, configured as a computing system, for a modular human surrogate.

FIG. 12 shows an example computing device 600 (e.g., a computer) that may be arranged in some embodiments to perform the methods (or portions thereof) described herein. In a very basic configuration 602, computing device 600 generally includes one or more processors 604 and a system memory 606. A memory bus 608 may be used for communicating between processor 604 and system memory 606.

Depending on the desired configuration, processor 604 may be of any type including, but not limited to: a microprocessor ($0^3$), a microcontroller (µC), a digital signal processor (DSP), or any combination thereof. Processor 604 may include one or more levels of caching, such as a level one cache 610 and a level two cache 612, a processor core 614, and registers 616. An example processor core 614 may include an arithmetic logic unit (ALU), a floating point unit (FPU), a digital signal processing core (DSP Core), or any combination thereof. An example memory controller 618 may also be used with processor 604, or in some implementations, memory controller 618 may be an internal part of processor 604.

Depending on the desired configuration, system memory 606 may be of any type including, but not limited to: volatile memory (such as RAM), non-volatile memory (such as ROM, flash memory, etc.), or any combination thereof. System memory 606 may include an operating system 620, one or more applications 622, and program data 624. Application 622 may include a determination application 626 that is arranged to perform the operations as described herein, including those described with respect to methods described herein. The determination application 626 can obtain data, such as pressure, flow rate, and/or temperature, and then determine a change to the system to change the pressure, flow rate, and/or temperature.

Computing device 600 may have additional features or functionality, and additional interfaces to facilitate communications between basic configuration 602 and any required devices and interfaces. For example, a bus/interface controller 630 may be used to facilitate communications between basic configuration 602 and one or more data storage devices 632 via a storage interface bus 634. Data storage devices 632 may be removable storage devices 636, non-removable storage devices 638, or a combination thereof. Examples of removable storage and non-removable storage devices include: magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include: volatile and non-volatile, removable and non-removable media implemented in any method or technology for storage of information, such as computer readable instructions, data structures, program modules, or other data.

System memory 606, removable storage devices 636 and non-removable storage devices 638 are examples of computer storage media. Computer storage media includes, but is not limited to: RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 600. Any such computer storage media may be part of computing device 600.

Computing device 600 may also include an interface bus 640 for facilitating communication from various interface devices (e.g., output devices 642, peripheral interfaces 644, and communication devices 646) to basic configuration 602 via bus/interface controller 630. Example output devices 642 include a graphics processing unit 648 and an audio processing unit 650, which may be configured to communicate to various external devices such as a display or speakers via one or more A/V ports 652. Example peripheral interfaces 644 include a serial interface controller 654 or a parallel interface controller 656, which may be configured to communicate with external devices such as input devices (e.g., keyboard, mouse, pen, voice input device, touch input device, etc.) or other peripheral devices (e.g., printer, scanner, etc.) via one or more I/O ports 658. An example communication device 646 includes a network controller 660, which may be arranged to facilitate communications with one or more other computing devices 662 over a network communication link via one or more communication ports 664.

The network communication link may be one example of a communication media. Communication media may generally be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR), and other wireless media. The term computer readable media as used herein may include both storage media and communication media.

Computing device 600 may be implemented as a portion of a small-form factor portable (or mobile) electronic device such as a cell phone, a personal data assistant (PDA), a personal media player device, a wireless web-watch device, a personal headset device, an application specific device, or a hybrid device that includes any of the above functions. Computing device 600 may also be implemented as a personal computer including both laptop computer and non-laptop computer configurations. The computing device 600 can also be any type of network computing device. The computing device 600 can also be an automated system as described herein.

The embodiments described herein may include the use of a special purpose or general-purpose computer including various computer hardware or software modules.

Embodiments within the scope of the present invention also include computer-readable media for carrying or having computer-executable instructions or data structures stored thereon. Such computer-readable media can be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium which can be used to carry or store desired program code means in the form of computer-executable instructions or data structures and which can be accessed by a general purpose or special purpose computer. When information is transferred or provided over a network or another communications connection (either hardwired, wireless, or a combination of hardwired or wireless) to a computer, the computer properly views the connection as a computer-readable medium. Thus, any such connection is properly termed a computer-readable medium. Combinations of the above should also be included within the scope of computer-readable media.

Computer-executable instructions comprise, for example, instructions and data which cause a general purpose computer, special purpose computer, or special purpose processing device to perform a certain function or group of functions. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation, no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general, such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

All references recited herein are incorporated herein by specific reference in their entirety.

The invention claimed is:

1. A surrogate system comprising:
a first body having an external body surface with an anatomical shape of a head configured as a head module, wherein the first body includes an internal chamber with at least one port formed in the first body extending inwardly from the external body surface;
a second body having an anatomical shape of a torso configured as a torso module that is coupled with the head module;
at least one anatomical module having an anatomical module body with an external module portion and an internal module portion coupled to the external module portion, the internal module portion of the anatomical module body being shaped to be removably received into the at least one port, the external module portion having an external module surface with a partial anatomical shape so that the external body surface matches with the external module surface to provide a continuous anatomical shape;
at least one sensor located in the at least one anatomical module; and
at least one controller, wherein the at least one sensor is configured to be operably coupled with the at least one controller.

2. A method of monitoring a non-lethal exposure with a surrogate system, comprising:
providing the surrogate system of claim 1;
determining at least one stimulus of the non-lethal exposure;
configuring the surrogate system with the at least one sensor, which is configured for measuring the at least one stimulus, wherein the at least one anatomical module is in the at least one port;
exposing the surrogate system to the at least one stimulus;
measuring the at least one stimulus with the at least one sensor to obtain stimulus data; and
recording the stimulus data with the controller.

3. A method of developing a non-lethal weapon with a surrogate system, comprising:
providing the surrogate system of claim 1;
providing the non-lethal weapon;
determining at least one stimulus of the non-lethal weapon;
configuring the surrogate system with the at least one sensor, which is configured for measuring the at least one stimulus, wherein the at least one anatomical module is in the at least one port;
exposing the surrogate system to the at least one stimulus;
measuring the at least one stimulus with the at least one sensor to obtain stimulus data; and
recording the stimulus data with the controller.

4. The surrogate system of claim 1, further comprising a brain module having at least one sensor, the brain module being located in the internal chamber.

5. The surrogate system of claim 1, further comprising a neck stem configured to be coupled with the head module and torso module so as to link the head module with the torso module.

6. The surrogate system of claim 1, wherein the at least one anatomical module is configured as at least one of: an eye module; an ear module; a nose module; or a mouth module.

7. The surrogate system of claim 1, wherein the at least one controller includes a processor and a memory device having instructions that when executed by the processor causes collection and/or processing of stimuli data from the at least one sensor.

8. The surrogate system of claim 7, wherein the instructions cause at least one of:
the processor to save the stimuli data on a data memory device; or
the processor to transmit the stimuli data to an external computing system.

9. The surrogate system of claim 7, wherein the at least one anatomical module is coupled by at least one of the following:
electrically coupled with the at least one controller;
optically coupled with the at least one controller; or
wirelessly coupled with the at least one controller.

10. The surrogate system of claim 7, wherein the at least one controller is configured for at least one of:
record stimuli data from the at least one sensor in real time; or
correlate stimuli data from the at least one sensor with a real human response to the stimuli input into the sensor that causes formation of the stimuli data.

11. The surrogate system of claim 1, wherein the at least one sensor comprises a plurality of sensors that includes a first sensor for measuring a first type of stimuli and a second sensor for measuring a second type of stimuli, wherein the first type of stimuli is different from the second type of stimuli.

12. The surrogate system of claim 1, wherein the at least one sensor is selected from a pressure sensor, sound sensor, light sensor, electrical sensor, temperature sensor, or blunt force sensor.

13. The surrogate system of claim 1, wherein the external body surface and/or external module surface include a surrogate skin layer.

14. The surrogate system of claim 13, wherein the head module has a skull assembly covered by a skin surrogate layer.

15. A method of testing exposure to a stimulus, the method comprising:
providing the surrogate system of claim 1, wherein the at least one anatomical module is in the at least one port;
exposing the surrogate system to at least one stimulus;
measuring the at least one stimulus with the at least one sensor to obtain stimulus data; and
recording the stimulus data with the controller.

16. The method of claim 15, further comprising:
determining the at least one stimulus to be measured; and
preparing the surrogate system such that the at least one sensor measures the at least one stimulus.

17. The method of one claim 15, wherein the at least one stimulus is at least one of: sound, light, heat, blunt impact, pressure, or electro-muscular stimulation.

18. The method of claim 15, further comprising:
exposing the surrogate system to a plurality of stimuli;
measuring the plurality of stimuli with a plurality of sensors to obtain stimuli data, wherein the surrogate system includes the plurality of sensors in the at least one anatomical module; and
recording the stimuli data with the controller.

19. The method of one claim 15, further comprising at least one of:
recording the stimulus data in real time;
correlating the stimulus data with a living human response to the at least one stimulus;
transmitting the stimulus data from the controller to an external computing system;
storing the stimulus data on a storage medium of the controller; or
setting the surrogate system to measure the at least one stimulus.

20. The method of claim 15, comprising:
determining a first sensor of the at least one sensor to be malfunctioning; and
replacing the malfunctioning first sensor with a functional first sensor.

21. The method of claim 15, comprising:
removing a first anatomical module of the at least one anatomical module with a first sensor of the at least one sensor from a first port of the at least one port of the surrogate system; and
installing a second anatomical module with a second sensor in the first port of the surrogate system.

22. A surrogate system comprising:
a body having an external body surface with an anatomical, wherein the body includes an internal chamber with at least one port formed in the body extending inwardly from the external body surface;
at least one anatomical module having an anatomical module body with an external module portion and an internal module portion coupled to the external module portion, the internal module portion of the anatomical module body being shaped to be removably received into the at least one port, the external module portion having an external module surface with a partial anatomical shape so that the external body surface matches with the external module surface to provide a continuous anatomical shape, wherein the at least one anatomical module is configured as at least one of: an eye module; an ear module; a nose module; a mouth module; or a chest plate module;
at least one sensor located in the at least one anatomical module; and
at least one controller, wherein the at least one sensor is configured to be operably coupled with the at least one controller.

23. A surrogate system comprising:
a body having an external body surface with an anatomical, wherein the body includes an internal chamber with at least one port formed in the body extending inwardly from the external body surface;
at least one anatomical module having an anatomical module body with an external module portion and an internal module portion coupled to the external module portion, the internal module portion of the anatomical module body being shaped to be removably received into the at least one port, the external module portion having an external module surface with a partial anatomical shape so that the external body surface matches with the external module surface to provide a continuous anatomical shape, wherein the at least one anatomical module is in the at least one port of the body to form the continuous anatomical shape;

at least one sensor located in the at least one anatomical module; and at least one controller, wherein the at least one sensor is configured to be operably coupled with the at least one controller.

24. A surrogate system comprising:

a body having an external body surface with an anatomical shape, wherein the body includes an internal chamber with at least one port formed in the body extending inwardly from the external body surface;

at least one anatomical module having an anatomical module body with an external module portion and an internal module portion coupled to the external module portion, the internal module portion of the anatomical module body being shaped to be removably received into the at least one port, the external module portion having an external module surface with a partial anatomical shape so that the external body surface matches with the external module surface to provide a continuous anatomical shape;

a brain module having at least one sensor, the brain module being located in the internal chamber, and the anatomical shape is a head shape;

at least one sensor located in the at least one anatomical module; and at least one controller, wherein the at least one sensor is configured to be operably coupled with the at least one controller.

* * * * *